(12) United States Patent
Neas et al.

(10) Patent No.: US 9,283,202 B2
(45) Date of Patent: Mar. 15, 2016

(54) STABLE PERACID-CONTAINING COMPOSITIONS

(71) Applicant: CHD Bioscience, Inc., Fort Collins, CO (US)

(72) Inventors: Edwin D. Neas, Nunn, CO (US); Michael K. Handley, Windsor, CO (US); Kevin S. Marchitto, Golden, CO (US); Stephen T. Flock, Arvada, CO (US); Charles Henry, Fort Collins, CO (US)

(73) Assignee: CHD Bioscience, Inc., Ft. Collins, CO (US)

( * ) Notice: Subject to any disclaimer, the term of this patent is extended or adjusted under 35 U.S.C. 154(b) by 0 days.

(21) Appl. No.: 14/058,063

(22) Filed: Oct. 18, 2013

(65) Prior Publication Data

US 2014/0113967 A1 Apr. 24, 2014

Related U.S. Application Data

(60) Provisional application No. 61/715,725, filed on Oct. 18, 2012.

(51) Int. Cl.

| A61K 31/327 | (2006.01) |
| A01N 37/16 | (2006.01) |
| A01N 37/42 | (2006.01) |
| A61K 45/06 | (2006.01) |
| A01N 25/02 | (2006.01) |
| A01N 37/36 | (2006.01) |
| D06L 3/02 | (2006.01) |
| A61K 33/40 | (2006.01) |

(52) U.S. Cl.
CPC .............. *A61K 31/327* (2013.01); *A01N 25/02* (2013.01); *A01N 37/16* (2013.01); *A01N 37/36* (2013.01); *A01N 37/42* (2013.01); *A61K 33/40* (2013.01); *A61K 45/06* (2013.01); *D06L 3/021* (2013.01)

(58) Field of Classification Search
CPC .................................................... A61K 31/327
See application file for complete search history.

(56) References Cited

U.S. PATENT DOCUMENTS

| 2,806,045 A | 9/1957 | Gross |
| 3,169,986 A | 2/1965 | Reginald et al. |
| 3,829,468 A | 8/1974 | Serad et al. |
| 3,978,032 A | 8/1976 | Manner |
| 4,004,977 A | 1/1977 | Kato et al. |
| 4,008,175 A | 2/1977 | Barter |
| 5,597,791 A | 1/1997 | Richards et al. |
| 5,718,910 A | 2/1998 | Oakes et al. |
| 6,325,968 B1 | 12/2001 | Fricker et al. |
| 6,627,657 B1 | 9/2003 | Hilgren et al. |
| 6,943,190 B2 | 9/2005 | Fink et al. |
| 6,991,685 B2 | 1/2006 | Kravitz et al. |
| 8,349,449 B2 | 1/2013 | Privitera et al. |
| 8,426,634 B2 | 4/2013 | Neas et al. |
| 8,445,717 B2 | 5/2013 | Neas et al. |
| 2001/0016604 A1 | 8/2001 | Yu et al. |
| 2004/0176267 A1 | 9/2004 | Hobson et al. |
| 2005/0197397 A1 | 9/2005 | Martin |
| 2007/0048345 A1 | 3/2007 | Huang et al. |
| 2007/0056904 A1 | 3/2007 | Hogt et al. |
| 2007/0082832 A1 | 4/2007 | DiCosimo et al. |
| 2007/0148214 A1 | 6/2007 | Cullen et al. |
| 2007/0202069 A1 | 8/2007 | Tamareselvy et al. |
| 2008/0233069 A1 | 9/2008 | Tamareselvy et al. |
| 2009/0145859 A1 | 6/2009 | Man et al. |
| 2009/0239947 A1 | 9/2009 | Dai et al. |
| 2009/0269324 A1* | 10/2009 | Herdt et al. ................. 424/94.4 |
| 2010/0040608 A1 | 2/2010 | Wahren-Herlenius et al. |
| 2010/0108942 A1 | 5/2010 | Man et al. |
| 2010/0125104 A1 | 5/2010 | Neas et al. |
| 2011/0117178 A1 | 5/2011 | Junginger |
| 2011/0165261 A1 | 7/2011 | Derby et al. |
| 2011/0301070 A1 | 12/2011 | Ochomogo et al. |
| 2011/0305872 A1 | 12/2011 | Li et al. |
| 2012/0021486 A1 | 1/2012 | Dinu et al. |
| 2012/0213835 A1 | 8/2012 | Neas et al. |
| 2013/0224307 A1 | 8/2013 | Neas et al. |
| 2013/0251820 A1 | 9/2013 | Neas et al. |
| 2013/0330397 A1 | 12/2013 | Neas et al. |

FOREIGN PATENT DOCUMENTS

| EP | 0320219 | 6/1989 |
| WO | WO 91/13058 | 9/1991 |
| WO | WO 93/01716 | 2/1993 |
| WO | WO 2006/093792 | 9/2006 |
| WO | WO 2007/018923 | 2/2007 |
| WO | WO 2010/059531 | 5/2010 |
| WO | WO 2011/129829 | 10/2011 |
| WO | WO 2012/112951 | 8/2012 |

OTHER PUBLICATIONS

Hydrogen Peroxide MSDS (2011).*
Tong Q, Xiao Q, Lim LT. Preparations and Properties of Pullulan-Alginate-Carboxymethylcellulose Blend Films. Food Research International. 2008; 41: 1007-1014.*
International Search Report for PCT/US13/65769 dated Apr. 17, 2014, 46 pages.
Bunton (1949) Nature 163:444 "Oxidation of α-Diketones and α-Keto-Acids by Hydrogen Peroxide".
Cooper, et al. (1983) Chem. Rev. 83:321-358 "Synthesis and Properties of the α-Keto Acids".
Desagher et al. (1997) The Journal of Neuroscience 17(23):9060-9067 "Pyruvate Protects Neurons against Hydrogen Peroxide-Induced Toxicity".
Estes et al. (2010) Expert Rev Anti Infect Ther 8(3):325-338 "Present and future therapeutic strategies for melioidosis and glanders" doi:10.1586/eri.10.4.

(Continued)

*Primary Examiner* — Paul Zarek
(74) *Attorney, Agent, or Firm* — Volpe and Koenig, P.C.

(57) ABSTRACT

Methods have been developed for incorporation of peracid compounds and related compositions into a non-aqueous medium. The peracid incorporated into the non-aqueous medium is stable and keeps its chemical and antimicrobial activity for extended durations. The non-aqueous medium may be removed just prior to or during application of the peracid.

25 Claims, 7 Drawing Sheets

(56) References Cited

OTHER PUBLICATIONS

European Search Report for 09828061.3 mailed Sep. 24, 2012, 7 pages.
Fink (2003) J Trauma Injury Infection Critical Care 54:S141-S143 "Ringer's Ethyl Pyruvate Solution: A Novel Resuscitation Fluid for the Treatment of Hemorrhagic Shock and Sepsis".
Fink (2007) Current Drug Targets 8:515-518 "Ethyl Pyruvate: A Novel Treatment for Sepsis".
Fink (2007) J Intern Med 261:349-362 "Ethyl pyruvate: a novel anti-inflammatory agent".
Greenspan (1947) Industrial and Engineering Chemistry 39:847-848 "Oxidation Reactions with Aliphatic Peracids" XP-002683108.
Hanson (1987) Department of Biological Sciences 64(7):591-595 "Decarboxylation of α-Keto Acids".
Holleman (1904) Recl. Trav. Chim. Pays-bas Belg. 23 (English Abstract).
International Search Report for PCT/US09/64450 dated May 31, 2010, 5 pages.
International Search Report for PCT/US10/31245 dated Jan. 21, 2011, 5 pages.
International Search Report for PCT/US12/25736 dated May 29, 2012, 1 page.
International Search Report for PCT/US13/54968 dated Jan. 14, 2014, 20 pages.
International Search Report for PCT/US13/65782 dated Feb. 19, 2014, 32 pages.
Lever and Mackenzie (2007) BMJ 335:879-883 "Sepsis: definition, epidemiology, and diagnosis".
Miyaji et al. (2003) Kidney International 64:1620-1631 "Ethyl pyruvate decreases sepsis-induced acute renal failure and multiple organ damage in aged mice".
Nath et al. (1995) The American Physiological Society C227-C236 "α-Ketoacids scavenge $H_2O_2$ in vitro and in vivo and reduce menadione-induced DNA injury and cytotoxicity".
Neas et al. (2013) Power Point Presentation presented on Jan. 3, 2013 for U.S. Appl. No. 12/618,605 "CHD Bioscience: Answers for infectious disease: CHD Meeting with USPTO" 31 slides.
North Cell Pharm pamphlet "Effect of Alpha Keto Acids Including Sodium Pyruvate on Reducing and Regulating the Inflammatory Agents Needed in the Healing of Infected and Non-Infected Wounds" [retrieved on Jan. 29, 2014 from http://www.northcellpharma.com/NCP_Research_Devel_Data.pdf].
Panda and Patnaik (2001) Bull. Korean Chem. Soc. 22(8):909-913 "Peroxy Acid Oxidations: A Kinetic and Mechanistic Study of Oxidative Decarboxylation of α-Keto Acids by Peroxomonophosphoric Acid".
Swern (1948) Eastern Regional Research Laboratory 1-68 "Organic Peracids".
Vlachou and Berth-Jones (2007) Journal of Dermatological Treatment 18:175-177 "Nail psoriasis improvement in a patient treated with fumaric acid esters".
Vlessis et al. (1990) Biochemical and Biophysical Research Communications 170(3):1281-1287 "Importance of Spontaneous α-Ketoacid Decarboxylation in Experiments Involving Peroxide".
Wang et al. (1999) Science 285:248-251 "HMG-1 as a Late Mediator of Endotoxin Lethality in Mice".
Chen et al., Extracellular HMGB1 as a Proinflammatory Cytokine, Journal of Interferon & Cytokine Research, 24:329-33 (2004).

* cited by examiner

STABLE PERACID-CONTAINING COMPOSITIONS

RELATED APPLICATIONS

This application claims priority to U.S. Provisional Patent Application No. 61/715,725, filed Oct. 18, 2012, which is incorporated herein by reference in its entirety.

TECHNICAL FIELD

The present invention relates to methods and compositions for stabilizing peracid compositions in non-aqueous media.

BACKGROUND

Aqueous solutions of peracids have many industrial uses including, but not limited to, wide spectrum antimicrobial and biocidal properties. Aqueous peracid solutions are susceptible to decomposition, particularly at high temperatures, at alkaline pH values and in the presence of impurities, e.g. transition metal ions. The stability of aqueous peracetic acid solutions and other peracid solutions is typically improved by the addition of known hydrogen peroxide or peracid stabilizers. However, highly concentrated peracids in liquid form are very difficult to handle, are corrosive to the skin and are noxious. Highly concentrated peracid solutions may also present a fire and/or explosion hazard. Aqueous peracid solutions, even stabilized peracid solutions, are susceptible to decomposition losses in long term storage over weeks or months. Since ambient temperatures can vary widely, the presence of even very small amounts of impurities can have an adverse impact during long term storage.

There remains a need for highly stable and easy-to-handle peracid compositions that maintain their peracid chemical and antimicrobial activity during long term storage.

The present invention is directed toward overcoming one or more of the problems discussed above.

SUMMARY OF THE EMBODIMENTS

Methods have been developed for incorporation of peracid compounds and related compositions into a non-aqueous medium. The peracid incorporated into the non-aqueous medium is stable, and keeps its chemical and antimicrobial activity extended for longer periods of time. The non-aqueous medium may be removed just prior to or during application of the peracid.

Various modifications and additions can be made to the embodiments discussed without departing from the scope of the invention. For example, while the embodiments described above refer to particular features, the scope of this invention also included embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings.

DETAILED DESCRIPTION

Figure 1:
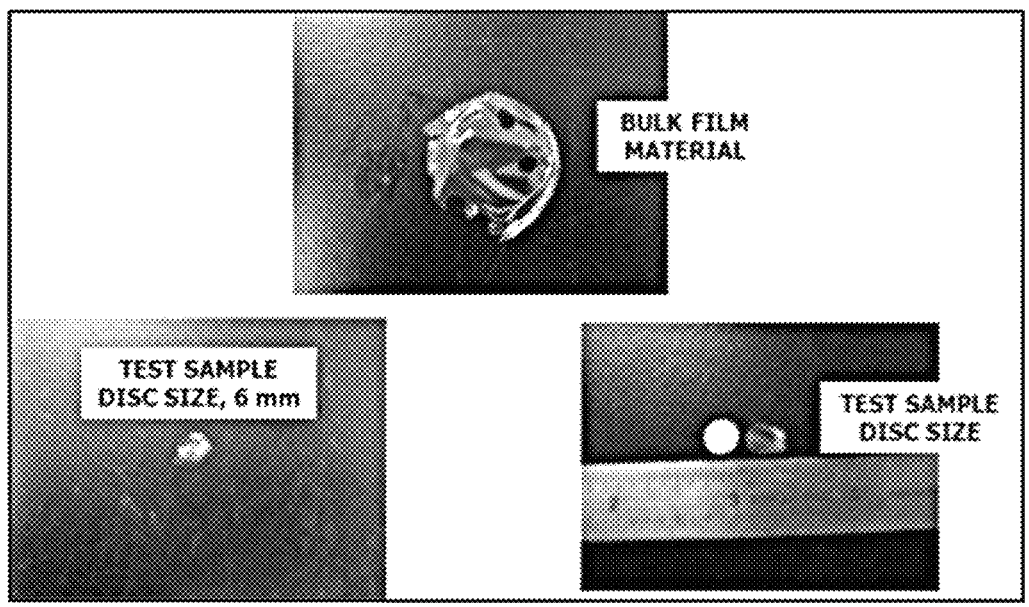
FIG. 1 is pullulan film impregnated with a peroxy pyruvic acid compound and a control film without a PPA compound.

While various aspects and features of certain embodiments have been summarized above, the following detailed description illustrates a few embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers expressing quantities of ingredients, dimensions, reaction conditions, and so forth, used in the specification and claims, are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

A means to stabilize the chemical and anti-microbial activity of peracids and peracid-containing compositions is described. Generally, the peracid may be impregnated, suspended in, or attached to a non-aqueous medium, and stored for extended periods while retaining chemical and antimicrobial activity.

In general, peracids are compounds of the oxidized form of a base organic acid (generally a carboxylic acid) that exist in equilibrium with an oxidizer (generally hydrogen peroxide) and water, as shown in Scheme 1. One species of peracid with superior antimicrobial properties are peroxy alpha-keto acid (PKCA) compounds (see U.S. patent application Ser. No. 13/400,013). PKCA compounds would generally be composed of an alpha-keto carboxylic acid, the anion of that alpha-keto acid, a buffer, hydrogen peroxide, and the oxidized form of the carboxylic acid. A peroxy pyruvic acid (PPA), for example, may be in equilibrium with pyruvic acid and hydrogen peroxide, as shown in Scheme 1. Moreover, excipients such as ethyl pyruvate may be added. Peracids may be oxidized from other carboxylic acids, e.g. citric acid, succinic acid, short chain fatty acids, etc. . . .

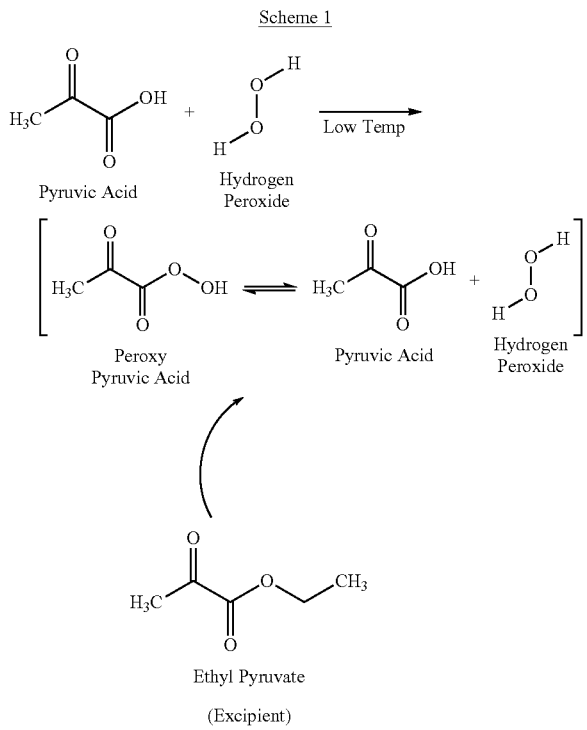

Scheme 1

Examples of non-aqueous media that may be capable of stabilizing peracids and peracid compositions include films, powders, gels, meshes, colloids, liposomes, micelles, or carbon nanostructures.

In some embodiments, the non-aqueous medium comprises polymers derived from plants, microorganisms or animals, microorganism-type polymers and animal-type polymers. A plant-derived polymer may be gum arabic, gum tragacanth, galactan, guar gum, carob gum, karaya gum, carrageenan, pectin, agar, quince seed or Cydonia oblonga, algae colloids such as brown algae extract, starches such as rice, corn, potato, or wheat, and glycyrrhizic acid. Microorganism-derived polymers may be xanthan gum, dextran, succinoglucan, and pullulan. Animal-derived polymers may be collagen, casein, albumin, and gelatin.

In some embodiments, the film-forming agent used in the films can be selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof.

A preferred embodiment is a dissolvable film comprised of a complex polysaccharide, such as pullulan, along with a plasticizer, such as lambda carrageenan.

The film may be formed from pullulan in amounts ranging from about 0.01 to about 99 wt. %, preferably about 30 to about 80 wt. %, more preferably from about 45 to about 70 wt. % of the film, and even more preferably from about 60 to about 65 wt. % of the film.

The non-aqueous media may optionally comprise in part or in whole a hydrocolloid. In some embodiments, the hydrocolloid comprises a water soluble natural polysaccharide or derivatives, including pectin and derivatives, guar gum arabic, tragacanth gum, xanthan gum, gellan sodium salt, propyleneglycol alginate, starches (amylose, amylopectin), modified starches, hydroxyethyl starch, pullulan, carboxymethyl starch, gum ghatti, okra gum, karaya gum, dextrans, dextrins and maltodextrins, konjac, acemannan from aloe, locust bean gum, tara gum, quince seed gum, fenugreek seed gum, scleroglucan, gum arabic, psyllium seed gum, tamarind gum, oat gum, quince seed gum, carrageenans, scleraglucan, succinoglucan, larch arabinogalactan, flaxseed gum, chondroitin sulfates, hyaluronic acid, curdlan, chitosan, deacetylated konjac, and rhizobium gum.

The hydrocolloid may be a water soluble non-gelling polypeptide or protein exemplified by gelatins, albumins, milk proteins, soy protein, and whey proteins. The hydrocolloid may further be selected from a group of synthetic hydrocolloids exemplified by polyethylene-imine, hydroxyethyl cellulose, sodium carboxymethyl cellulose, carboxymethyl cellulose, hydroxypropyl cellulose, hydroxypropyl methyl cellulose, methyl cellulose, ethyl cellulose, polyacrylic acids, low molecular weight polyacrylamides and their sodium salts (carbomers), polyvinylpyrrolidone, polyethylene glycols, polyethylene oxides, polyvinyl alcohols, pluronics, tetronics, and other block co-polymers, carboxyvinyl polymers, and colloidal silicon dioxide.

Suitable hydrocolloids or mixtures producing synergistic properties comprise natural seaweeds, natural seed gums, natural plant exudates, natural fruit extracts, biosynthetic gums, gelatines, biosynthetic processed starch or cellulosic materials, alginates, agar gum, guar gum, locust bean gum (carob), carrageenan, tara gum, gum arabic, ghatti gum, Khaya grandifolia gum, tragacanth gum, karaya gum, pectin, arabian (araban), xanthan, gellan, starch, Konjac mannan, galactomannan, funoran, are xanthan, acetan, gellan, welan, rhamsan, furcelleran, succinoglycan, scleroglycan, schizophyllan, tamarind gum, curdlan, pullulan, and dextran.

The non-aqueous peracid composition may be stored at room temperature or in a refrigerator, preferably in a light-tight container as the material can photodegrade in the presence of light, especially ultraviolet. The non-aqueous peracid composition is stable after a long period of time. Long term storage stability refers to the non-aqueous peracid composition's retaining their chemical activity over extended periods of time, e.g. over twelve months. The composition of the present invention provides non-aqueous peracids that exhibit unusually good storage stability retaining at least 60% of the initial peracid concentration for at least twelve months.

The peracid compositions have wide applicability as a disinfecting, sterilizing, biocidal or antimicrobial agent in both commercial and consumer applications. Commercial or industrial applications include food and beverage processing, pharmaceutical and medical industries, industrial waste water, and use as a bleaching agent in the textile and pulp and paper industries. Consumer applications include laundry and bleaching uses.

In some embodiments, it is desirable to remove the film polymer just prior to or during application of peracids. The polymer dissolves upon contact with fluids, thereby releasing peracids. In one embodiment, the polymer may be separated from peracids by boronic acids prior to or during application of peracids.

As a carbohydrate polymer, pullulan may be removed from the solution by a boronic acid modified resin. To create a carbohydrate-removal system, the capture resin would first be modified with a boronic acid. A wide range of resins would be appropriate ranging from silica to organic polymer in fundamental chemistry. The immobilization chemistry is also not specific, but should allow linkage of the boronic acid species without altering the boronic acid functionality. In one embodiment, Toyopearl AF-Carboxy-650 resin particle is used as a resin, 1-ethyl-3-(3-dimethylamino-propyl)carbodiimide (EDC) as a cross-linking agent, and 4-aminophenylboronic acid as the capture agent. These three reagents can be mixed together in a water based synthesis protocol to yield boronic acid modified resin.

Once the resin is modified, it could be packed into a column format where sample containing carbohydrates would be pulled through the resin before being dispensed. In one embodiment, a small cartridge is loaded on the end of a tube that contains the resin. As liquid was pulled through the cartridge, the carbohydrate would react with the boronic acid and become immobilized. The remaining solution would flow through the rest of the tube for dispensing.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

EXAMPLES

The following examples are provided for illustrative purposes only and are not intended to limit the scope of the invention.

Examples of PPA Compound Formulations

Example 1

As shown in FIG. 1, 100 ppm and 1000 ppm PPA compound were formulated into pullulan. To test efficacy and stability of the incorporated PPA compound, six millimeter discs were cut out of the PPA treated matrices and placed onto a methicillin resistant *staphylococcus aureus* (MRSA) streaked blood agar plate. A control film matrix disc which did not contain the PPA compound was prepared as well. This method simulated the well-known minimum inhibitory concentration (MIC) test. The blood agar plates were incubated overnight at optimal temperature and then observed for microbial kill.

Example 2

Figure 2:
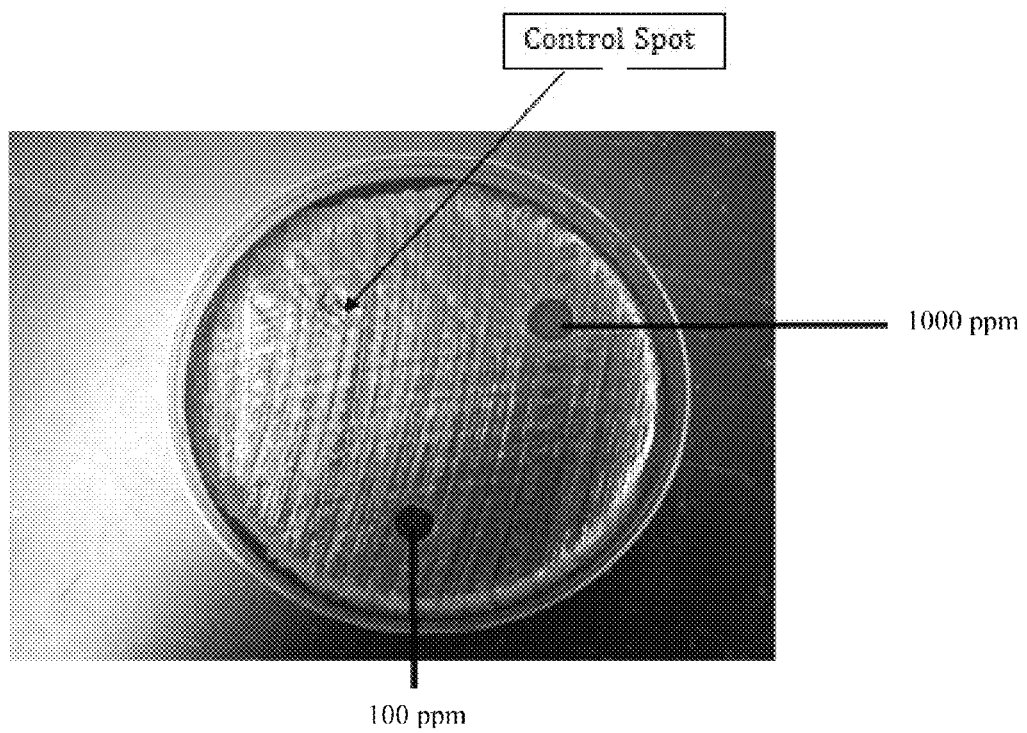
FIG. 2 is treatment of MRSA on blood agar plate with PPA compound incorporated in pullulan film.

As shown in FIG. 2, the blood agar plate was treated with pullulan containing the PPA compound at 100 ppm and 1000 ppm illustrated in FIG. 1 was observed for the diameter of bacteria kill the circle. The control film disc was the diameter of the grown of the 1000 ppm disc. The discs were placed on the blood agar plate and were dissolved by the moisture from the agar which allowed the PPA compound to migrate out of the film. The kill of MRSA was in proportion to the PPA concentration in the disc. Thus the 1000 ppm ratio of ppm concentration to the circle of kill diameter was greater than for the 100 ppm concentration to the circle diameter in millimeters. Calculations demonstrated that the proportionate diameters divided by the weight of the film was consistent with the expected concentrations. Other polymers can be coated with the stable solid-formulation of VERIOX and can later be released by exposure to water.

Example 3

Peracid Antimicrobial Efficacy after One Year of Storage

Figure 3:
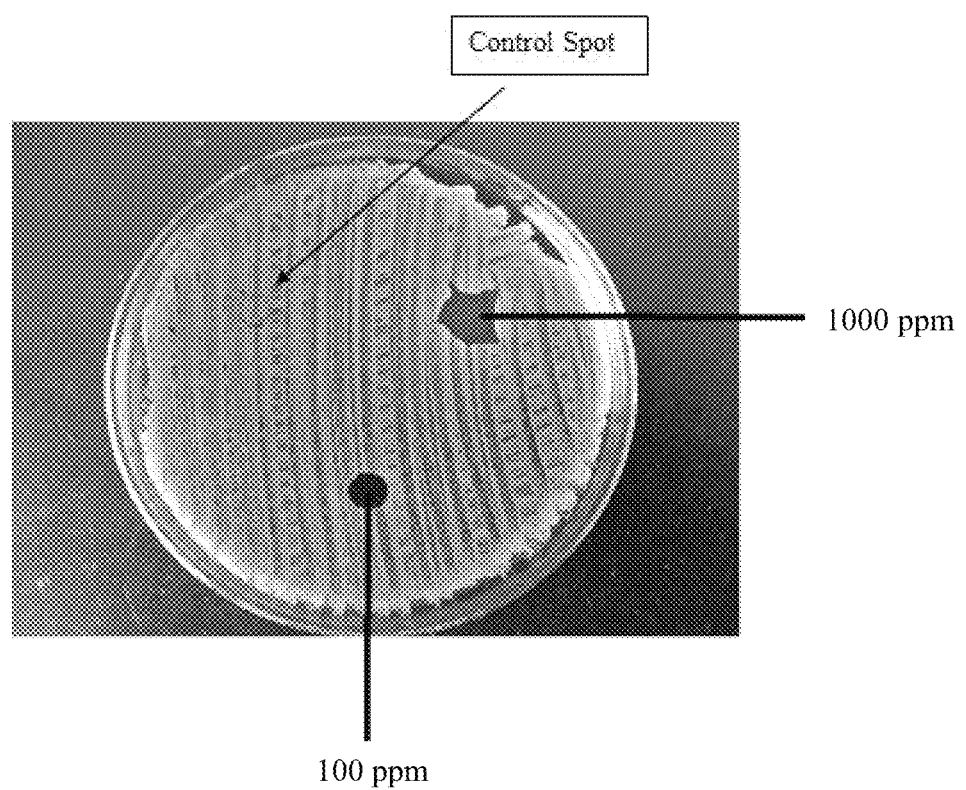
FIG. 3 is the blood agar plate was treated with the PPA-containing pullulan films made from 100 ppm and 1000 ppm PPA solution, as illustrated in FIG. 1, after one year storage.
Figure 4:
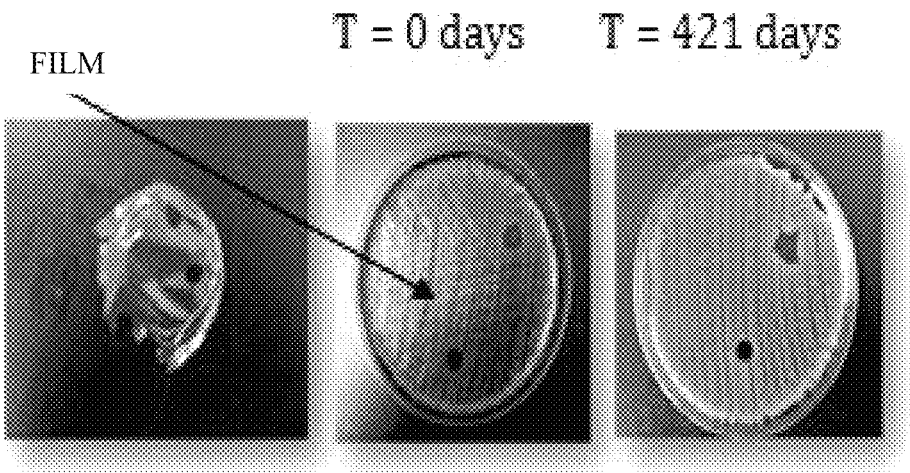
FIG. 4 is impregnated polymeric film with demonstrated anti-microbial properties at T=0 days and T=421 days.

FIGS. 3 and 4 show an example of 100 ppm and 1000 ppm PPA compound formulated into pullulan after one year of storage. The result shown in FIG. 3 is an example of treating MRSA on blood agar plate after one year of storage.

As shown in FIG. 4, the film after 421 days of storage still has chemical activity comparable to the newly made film.

Example 4

Dissolving Film Formulation

Formulations for the non-aqueous medium may include: 1. Fast-dissolving film component such as pullulan, generally 10-95% wt. %. 2. a plasticizer for flexibility such as λ-carrageenan, generally 0.05-35% wt. %. 3. a dissolution modulating agent (e.g. hydroxymethycellulose), generally 0.1%-10%, and 4. a surfactant, for dispersion, such as polysorbate A at 0.001-0.1%. The initial preparation is mixed in deionized water and cast. Final residual water content is generally 1-4% depending on method of casting and extent of drying.

The dissolvable medium may be made up of (wt./wt.) 2.09% pullulan, 0.087% λ-carrageenan, 0.14% polysorbate A and 160 ml of deionized water. A 9% peracid composition is added so that the concentration in the liquid peracid matrix is from 100 to 100,000 ppm. The final peracid concentration in the dried matrixes can be about 44 times greater than the concentration in the liquid matrix prior to dry-down.

The liquid film material is cast on a Teflon plate or releasable membrane, such as silicone rubber, allowed to dry in a sterile tissue-culture hood for 4-24 hours. Thickness of the film is determined by composition, and is affected as well by final moisture content which is further affected by the extent of the drawdown. The thicknesses can vary widely, but can be, for example, from about 20 to 200 microns.

Example 5

Pullulan Film Containing Peracid

All steps in this formulation were performed at room temperature. Measure out 103.9 ml of water and dispense into a 250 ml beaker with 1" magnetic stir bar. Begin stir at about 10 RPM. Keep beaker covered with aluminum foil to minimize evaporation.

Disperse 0.091 g λ-carrageenan slowly into water. Stir for no less than 30 minutes. Confirm that it's fully dispersed before going to the next step.

Measure out 2.18 g of pullulan and slowly dispense into beaker. Stir for no less than 15 minutes. A short time high-speed stirrer may be needed to get the material fully in contact with the water before reducing the speed.

Add 146 μl of polysorbate 80; continue to stir for 15 minutes. This volume of the highly viscous solution is difficult to measure with standard adjustable pipettors, so mass may be measured, and used a density of 1.075 g/ml to determine the volume dispensed. Add 1.17 ml of 1000 ppm pyruvate peracid ("PPA") to mixture and stir for several minutes.

In laminar flow hood, decant the following volumes into the molds in various sizes: 16.8 ml into each of 4 of 6×10 cm molds; 6.7 ml into 6×4 cm molds; 0.28 ml into 1×1 cm molds. All molds are 1.5 mm deep. Leave fan on and light off (patch drawdown is adversely affected by UV light) for at least 12 hours.

When the patches are dry, they release from the mold slightly. Sometimes they have to be coaxed off the silicone mold with tweezers.

Note that when the circular (1.875 inch diameter) patches dry down, they have a weight of about 0.15-0.25 g, and they started at about 5 g. Thus, assuming no peracid loss during drydown, the peracid concentration goes up about 20-30 fold.

The patches may be packed in sterile tin-foil, hand-crimped at the edges. This gives the fragile patch material some mechanical integrity. Store samples patches in 3M Scotchpak MB285 heat sealable polyester film laminate. Cut 9 inch length (6 inch fixed width) of film, fold over lengthwise and impulse seal on 3 edges (using 8" 450 W impulse bag sealer) for about ½ sec at each edge (setting on sealer=7). Insert patch and seal open edge. Then, the patch may be kept refrigerated.

The procedures apply to making films from 100 ppm to 96,000 ppm PPA solution.

Example 6

Removing Pullulan with a Boronic Acid Capture Resin

Figure 5:
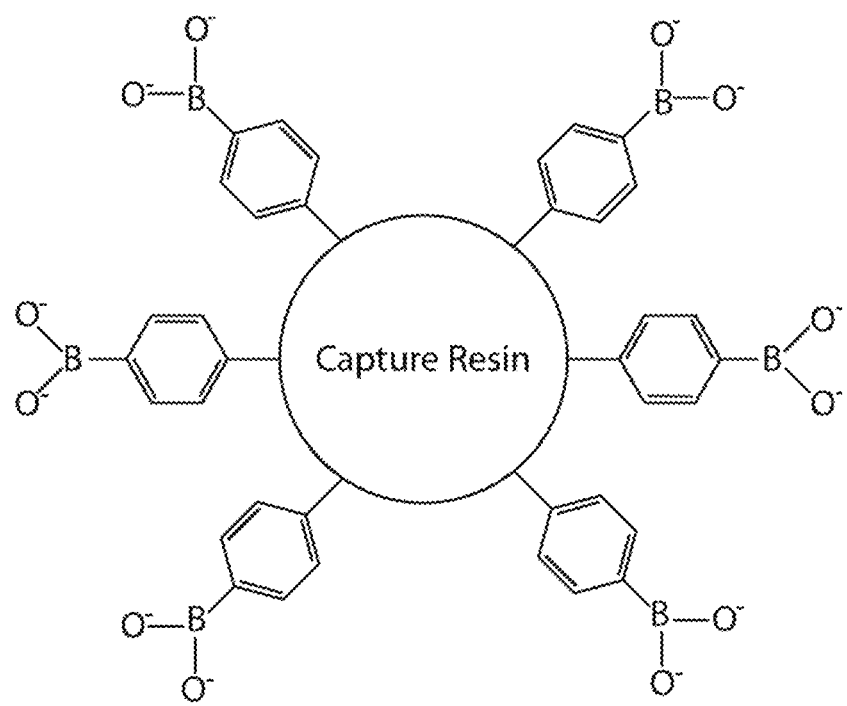
FIG. 5 is solid-phase capture resin modified with a phenyl boronic acid for removal of sugar residue.

FIG. 5 shows an example of boronic acid capture resin, one of several potential methods for pullulan removal. In this example, a polymeric resin is modified with a phenyl-boronic acid derivative such as 4-aminophenylboronic acid. The resin material is not specific and must simply have a surface functionality that allows for covalent attachment of the boronic acid species. Likewise, the specific boronic acid structure can be varied and only need contain a boronic acid and a functional element for immobilization on the capture resin. The method of immobilization is also not important and could be varied depending on the resin/boronic acid species. In addition to boronic acid, other resin materials could be utilized to achieve the same result, including but not limited to ion exchange, size exclusion and hydrophilic interaction resins.

Example 7

Removing Pullulan by Precipitation Using an Alcohol or PEG

Figure 6:
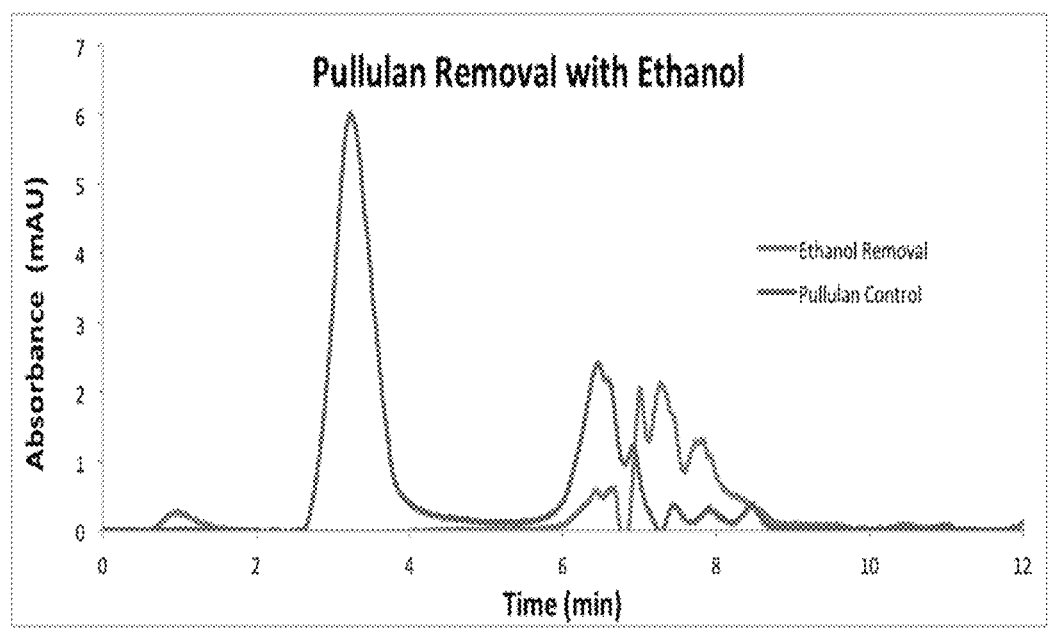
FIG. 6 is pullulan removal with ethanol.
Figure 7:
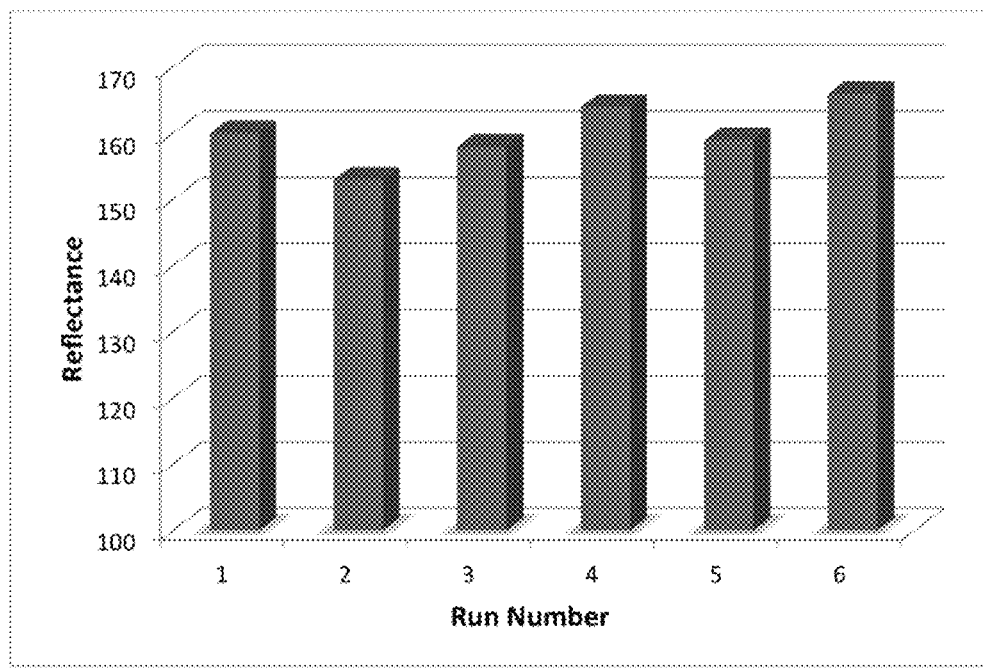
FIG. 7 is the measured concentration of active ingredient for pullulan removal using ethanol.
Figure 8:
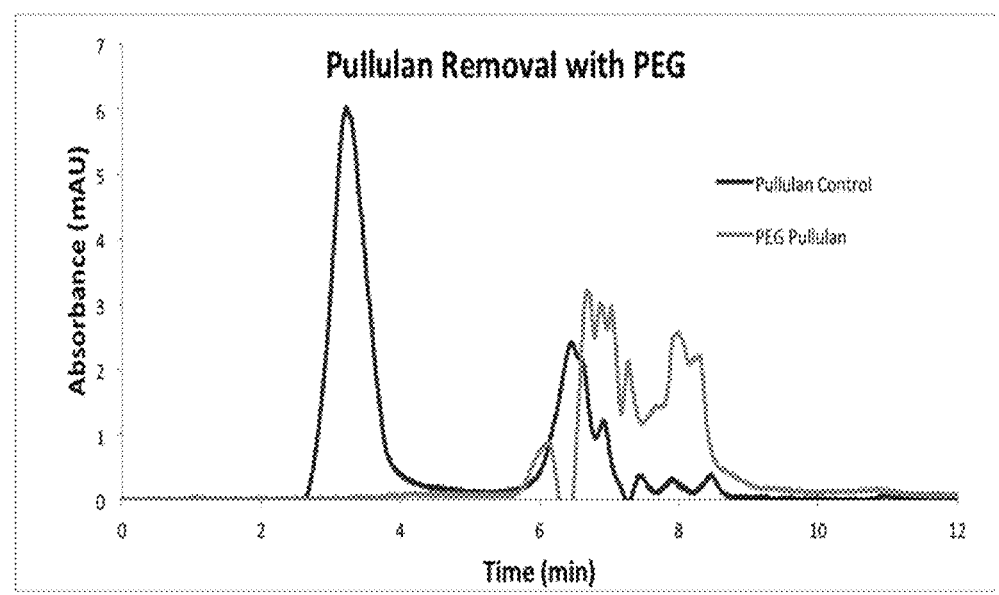
FIG. 8 is pullulan removal by PEG.

FIGS. 6-8 show examples of removing pullulan by precipitation using an alcohol or PEG. As an alternative, pullulan can be removed by precipitation using either an alcohol or polyethylene glycol (PEG). In this approach, the precipitating agent is added to the solution and causes pullulan to form a white solid. The active ingredient is not affected by this addition. The solid can be stopped from getting into the solution by either an appropriate container or a simple filter.

In some embodiments pullulan may be removed by adding an alcohol to precipitate the polymer.

FIG. 6 depicts an example of size exclusion chromatography with data showing the results for before and after addition of ethanol to a solution of pullulan. The "pullulan control" trace is the pullulan solution before addition of ethanol. The peak at 3 min is for the pullulan. The remaining peaks are for small molecules inherent in most solutions (fully retained species). After adding ethanol, the pullulan is precipitated. The resulting chromatogram is in blue, showing total removal of the pullulan from the solution.

As shown in FIG. 7, the precipitating agent does not impact the active ingredient. In FIG. 7, a 50% ethanol solution was prepared in buffer. The active ingredient concentration was measured over time for 25 minutes (one data point every five minutes). As shown in FIG. 7, there is no statistical difference across any of the measurements. Furthermore, measurements of the same concentration in straight buffer yield the same measured concentration of active ingredient.

FIG. 8 shows an example of pullulan removal by PEG. As shown in FIG. 8, in addition to ethanol, polyethylene glycol may be used to precipitate pullulan. FIG. 8 shows chromatograms from before and after addition of 2% PEG to a pullulan solution. As shown in FIG. 8, the "pullulan control" trace is for the pullulan. The "PEG pullulan" trace is for the pullulan after PEG addition.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

What is claimed is:

1. A stable peracid composition comprising a dissolvable non-aqueous medium and a peracid composition, the peracid composition comprising:
   a carboxylic acid;
   the peracid of said carboxylic acid;
   a peroxy α-ketocarboxylic acid; and
   an oxidizer,
   wherein the peracid composition is impregnated in, suspended in, or attached to the dissolvable non-aqueous medium.

2. The stable peracid composition according to claim 1, wherein the dissolvable non-aqueous medium further comprises a dissolvable polymer.

3. The stable peracid composition according to claim 1, wherein the dissolvable non-aqueous medium is in a form of film, pellets, granules, bars, powders, gels, meshes, colloids, liposomes, micelles, or carbon nanostructures.

4. The stable peracid composition according to claim 1, wherein the dissolvable non-aqueous medium is adapted to release the peracid composition upon contact of the stable peracid composition with water.

5. The stable peracid composition according to claim 4, wherein the dissolvable non-aqueous medium is adapted to be immobilized on a boronic acid capture resin when the stable peracid composition is exposed to the boronic capture resin and water.

6. The stable peracid composition according to claim 1, wherein the dissolvable non-aqueous medium is adapted to release the peracid composition upon contact of the stable peracid composition with an alcohol-based fluid.

7. The stable peracid composition according to claim 1, wherein the dissolvable non-aqueous medium is adapted to release the peracid composition upon contact of the stable peracid composition with polyethylene glycol, PEG.

8. The stable peracid composition according to claim 1, wherein the non-aqueous medium comprises pullulan.

9. A composition comprising:
   a dissolvable polymer;
   a carboxylic acid;
   the peracid of said carboxylic acid;
   a peroxy α-ketocarboxylic acid; and
   an oxidizer impregnated in the dissolvable polymer.

10. The composition according to claim 9, wherein the dissolvable polymer is in a form of a film, pellets, granules, bars, powders, gels, meshes, colloids, liposomes, micelles, or carbon nanostructures.

11. A method of stabilizing a peracid compound comprising:
    mixing the peracid compound with a dissolvable polymer in an aqueous solution; and
    drying the mixture to make a peracid-containing composition.

12. The method according to claim 11, wherein the peracid composition comprises a carboxylic acid, the peracid of said carboxylic acid, a peroxy α-ketocarboxylic acid and an oxidizer.

13. A method for sterilizing, disinfecting, or sanitizing hard or porous surfaces or fabrics comprising:
    dissolving a stable composition comprising a non-aqueous medium containing a film polymer, a carboxylic acid, the peracid of said carboxylic acid, a peroxy α-ketocarboxylic acid and an oxidizer;
    separating the non-aqueous medium from the peracid;
    removing the film polymer from the peracid; and
    applying the peracid on the surfaces or fabrics.

14. The method of claim 13, wherein the peracid is separated in the presence of polyethylene glycol.

15. The method of claim 13, wherein the peracid is separated in the presence of an alcohol.

16. The method of claim 13, wherein the peracid is separated in the presence of water.

17. The method of claim 13, wherein the film polymer is separated prior to the application of the peracid on surfaces, fabrics, or instruments.

18. The method of claim 13, wherein the separated peracid is applied on medical instruments, consumer products or industrial instruments for disinfection or sterilization.

19. The method of claim 13, wherein the separated peracid is applied on hard or porous surfaces for disinfection or sterilization.

20. The method of claim 13, wherein the separated peracid is applied on fabrics for disinfection or sterilization.

21. The stable peracid composition according to claim 1, wherein the carboxylic acid is acetic acid and the peracid of said carboxylic acid is peracetic acid.

22. The stable peracid composition according to claim 1, wherein the peroxy a-ketocarboxylic acid is peroxy pyruvic acid.

23. The stable peracid composition according to claim 1, wherein the oxidizer is hydrogen peroxide.

24. The stable peracid composition according to claim 2, wherein the dissolvable polymer is a mixture of pullulan and sodium alginate.

25. The stable peracid composition according to claim 2, wherein the dissolvable polymer is a mixture of pullulan and sodium alginate, the carboxylic acid is acetic acid and the peracid of said carboxylic acid is peracetic acid, the peroxy α-ketocarboxylic acid is peroxy pyruvic acid, and the oxidizer is hydrogen peroxide.

* * * * *